United States Patent [19]

Twisselmann

[11] Patent Number: 5,029,941
[45] Date of Patent: Jul. 9, 1991

[54] SURGEON'S CHAIR

[75] Inventor: Lorenz Twisselmann, Wedel/Holstein, Fed. Rep. of Germany

[73] Assignee: J. D. Moller Optische Werke GmbH, Wedel/Holstein, Fed. Rep. of Germany

[21] Appl. No.: 482,067

[22] Filed: Feb. 16, 1990

[30] Foreign Application Priority Data

Feb. 16, 1989 [DE] Fed. Rep. of Germany ....... 8901789
Mar. 14, 1989 [DE] Fed. Rep. of Germany ....... 8903118

[51] Int. Cl.⁵ .............................................. A47C 7/54
[52] U.S. Cl. .................................. 297/411; 297/345; 297/417
[58] Field of Search ............... 297/411, 415, 416, 417, 297/345, 347, 353, 115, 344

[56] References Cited

U.S. PATENT DOCUMENTS

| | | | |
|---|---|---|---|
| 3,222,105 | 12/1965 | Cross | 297/411 X |
| 4,025,112 | 5/1977 | Hale | 297/411 |
| 4,277,102 | 7/1981 | Aaras et al. | 297/411 |
| 4,452,487 | 6/1984 | Plowman | 297/411 |
| 4,533,106 | 8/1985 | Stöckl | 297/345 |
| 4,592,590 | 6/1986 | Slaats et al. | 297/347 |
| 4,729,601 | 3/1988 | Walle et al. | 297/344 |
| 4,749,230 | 6/1988 | Tornero | 297/353 |

Primary Examiner—Peter A. Aschenbrenner
Attorney, Agent, or Firm—Toren, McGeady & Associates

[57] ABSTRACT

In order to achieve an ergonomically and medically correct sitting position for the surgeon in every working position, the surgeon's chair is constructed in such a way that an adaptation to the frequently changing position of the surgeon is possible, for which purpose a vertically adjustable and horizontally displaceable seat is mounted on a column with a detachable backrest and with articulated arms with armrests arranged lattery to the seat and transferrable into various angular positions, in which chair the articulated arms are transferrable into optimal angles of inclination by means of two hinges and, over and above that, are transferrable as far as into the lateral area of the backrest when a sitting position facing the backrest has to be assumed.

10 Claims, 5 Drawing Sheets

1

SURGEON'S CHAIR

BACKGROUND OF THE INVENTION

The present invention relates to a surgeon's chair.

In respect of its construction, exacting requirements have to be met by a surgeon's chair in order to ensure the ergonomically and medically correct sitting of the surgeon in his respective working position.

That is why it is the object of the present invention to provide a surgeon's chair that meets all requirements with regard to an ergonomically and medically correct sitting in the respective working position of the surgeon, which can be adapted to frequently changing sitting positions of the surgeon and which can be converted in a versatile manner based on the modular system principle.

This technical problem is solved by the features characterized in the claim 1.

SUMMARY OF THE INVENTION

Such a surgeon's chair constructed according to the invention is unusually flexible and adaptable to the frequently varying sitting positions of the surgeon; it thus meets all the ergonomic requirements regarding sitting positions. The surgeon's chair with its technical solution determines a new concept inasmuch a modular design forms the basis of the surgeon's chair, the start being made from an inexpensive basic model. It is advantageous that the armrests of the surgeon's chair can be adjusted by the surgeon himself in a manner not known up till now under sterile conditions and, with that, be individually adapted. The vertically adjustable backrest is retained on the seating surface or seat of the surgeon's chair in such a way that a readjustment is possible so as to enable the backrest to be also employed as a frontrest, i.e. to provide support for the surgeon's chest. In particular by the electromotively effected vertical adjustment by means of a foot-operated switch, the surgeon's chair can be readily adjusted as to height. The horizontal displacement of the seat serves to optimize the position of the surgeon relative to the operating microscope and the position of the armrests relative to the operating area. In this case the release is preferably effected with the aid of a foot lever.

It is of particular advantage that the surgeon's chair consists of a basic extensible element comprising the upright column with base and seat. All further elements such as supporting bars, armrests, and the like can be added to the structure, likewise additional foot-operated switches, provided that such switches are already present. If the surgeon's chair is provided with lockable runners, the surgeon's chair is capable of effortless displacement; it may also be used as an individual chair and in connection with microscope carrying units.

BRIEF DESCRIPTION OF THE DRAWINGS

Advantageous embodiments of the invention are explained in greater detail in the following with the aid of the drawings. In diagrammatical views.

DETAILED DESCRIPTION OF THE PREFERRED EMBODIMENT

Figure 1:
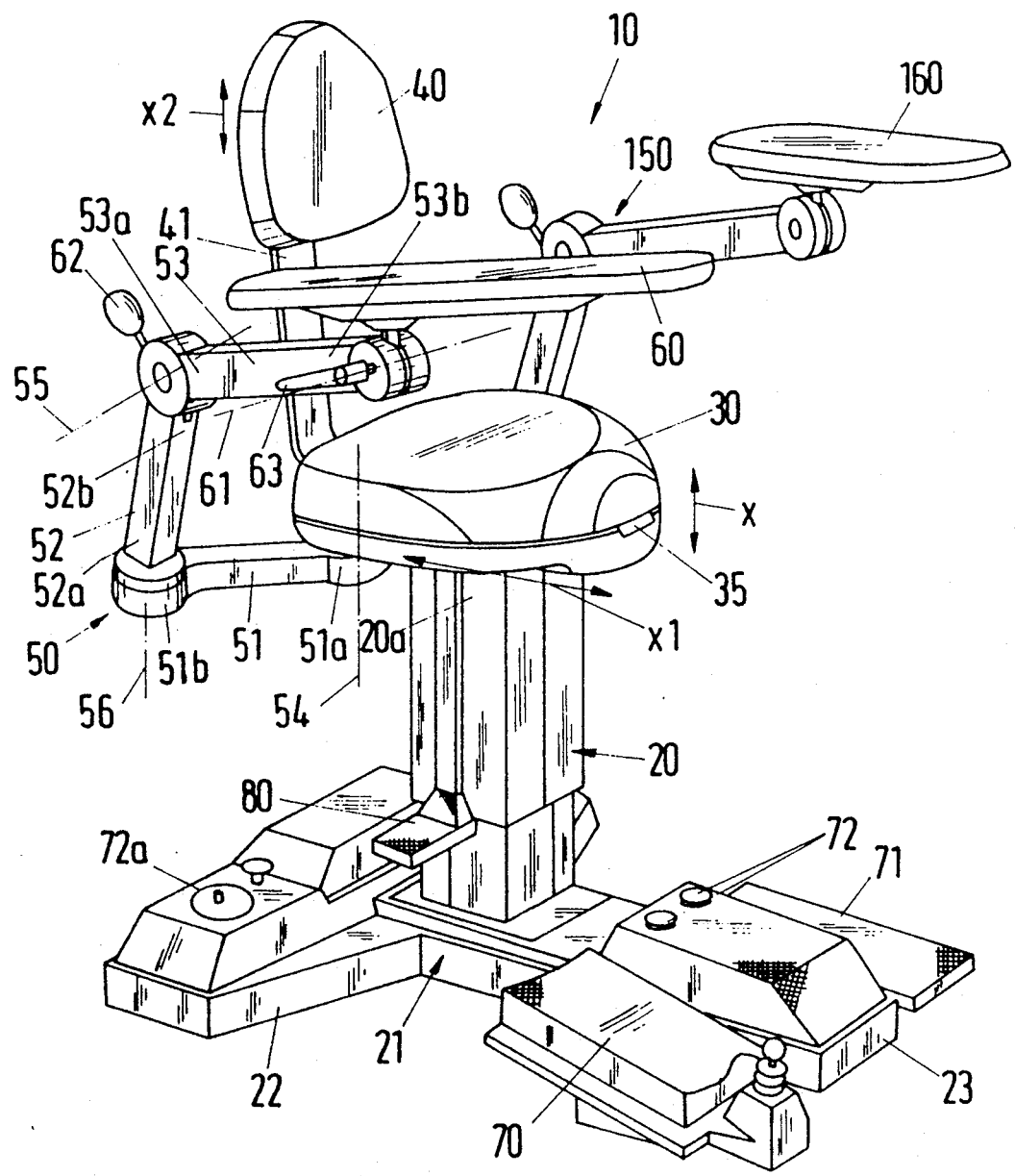
FIG. 1 shows the surgeon's chair.
Figure 2:
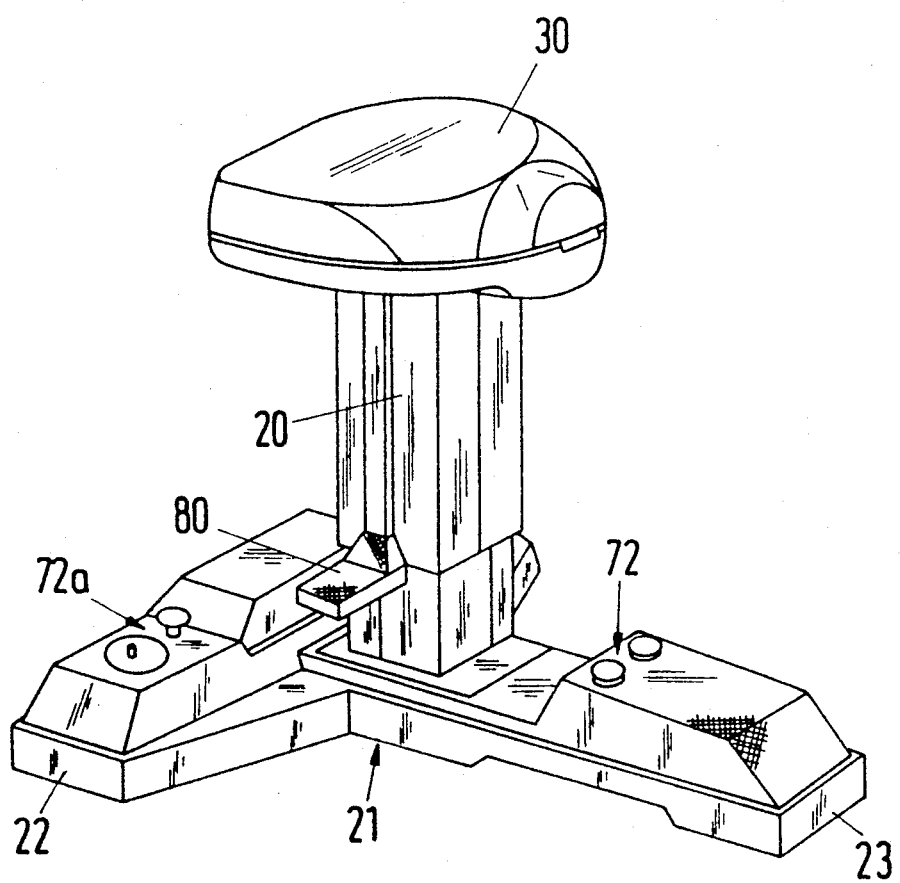
FIG. 2 shows the basic element of the surgeon's chair consisting of the seat, column and base.

The surgeon's chair depicted in its entirety in FIG. 1 and identified with 10 is constructed in a modular fashion and consists of a basic element shown in FIG. 2, which is formed by a vertical column 20, a T-shaped base 21 and a seat 30 that is vertically displaceable in the direction of arrow X and horizontally displaceable in the direction of arrow X1. The column 20 is arranged so as to stand vertically on the T-shaped base 21 which consists of a transverse bar 22 and a longitudinal bar 23, the column 20 being disposed on the longitudinal bar 23 adjacent to the connecting area of the transverse bar 22 with the longitudinal bar 23. The upper end 20a of the column 20 supports the seat 30. This seat 30 is vertically adjustable by mechanical or electromotive means, it being possible to control the operation of the vertical adjustability with the aid of the foot-operated switches 72. The vertical displaceability may also be effected by means of a safety gas spring, whereas the lowering is effected by loading with a weight and the cancellation of the gas spring pressure. However, an electromotive vertical adjustment is also possible.

The base 21 is provided with lockable runners so that, once having been appropriately fitted, the entire surgeon's chair can be easily replaced by the operating surgeon. In addition, the base is provided with a plurality of foot-operated and control switches, this will be dealt with in greater detail in the following.

The horizontal displacement of the seat 30 is effected by means of a horizontal guideway disposed on the upper end 20a of the column and not depicted in the drawing as well as by a carriage formed on the underside of the seat 30 that is slidingly retained in the guideway, while the horizontal displaceability of the seat 30 may likewise be effected by electromotive means, controlled by either a foot-operated switch or also mechanically. By the actuation of the pedal 80, the seat 30 can be adjusted in every displacement position. The electromotive drive means necessary for electromotively displacing the seat 30 are preferably accommodated in the column 20.

Figure 3:
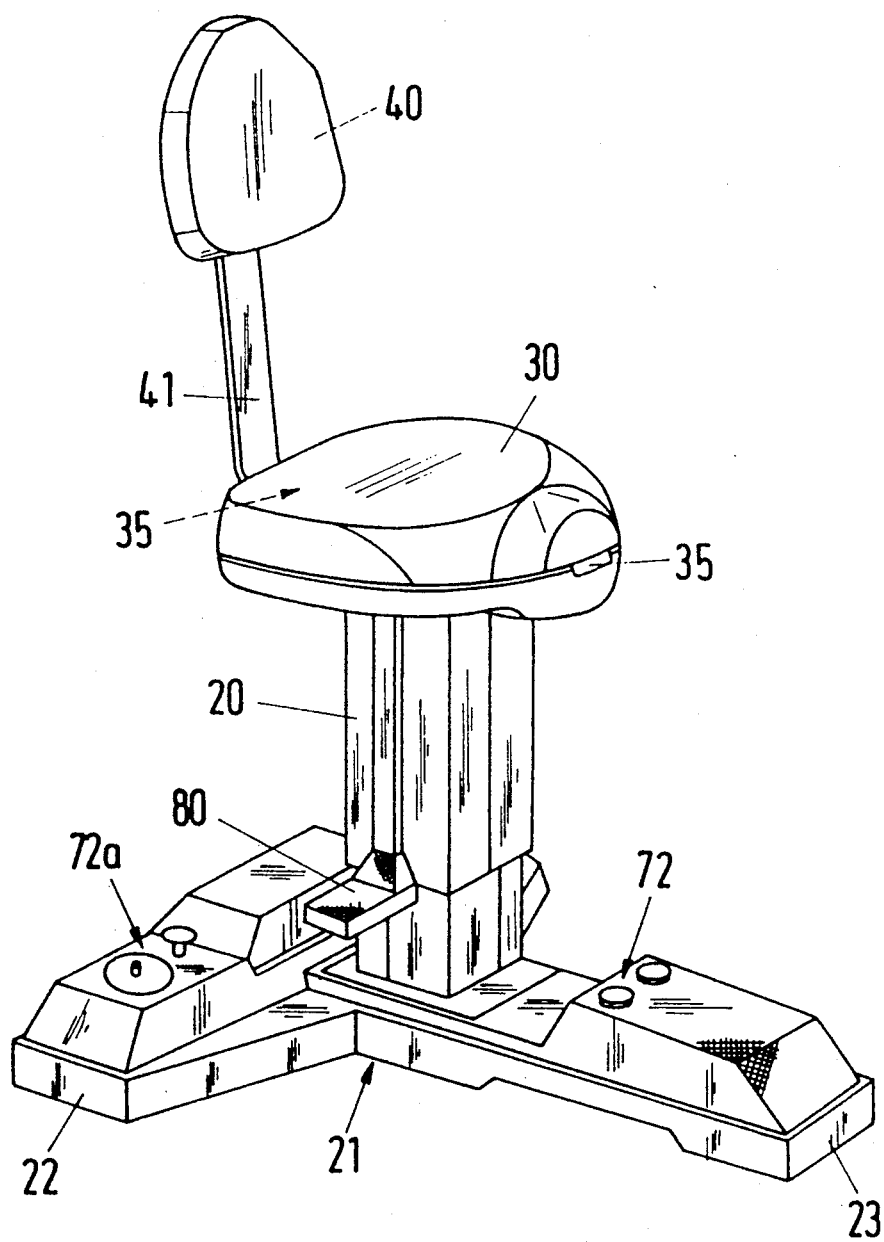
FIG. 3 shows the basic element of the surgeon's chair according to FIG. 2 extended by a backrest.

As is depicted in FIG. 3, the seat 30 is provided with a rearwardly mounted vertical supporting arm 41 which carries a backrest 40 that is vertically displaceable in the direction of arrow X2 by preferably mechanical means and can be locked in every position (FIGS. 1 and 3).

Figure 5:
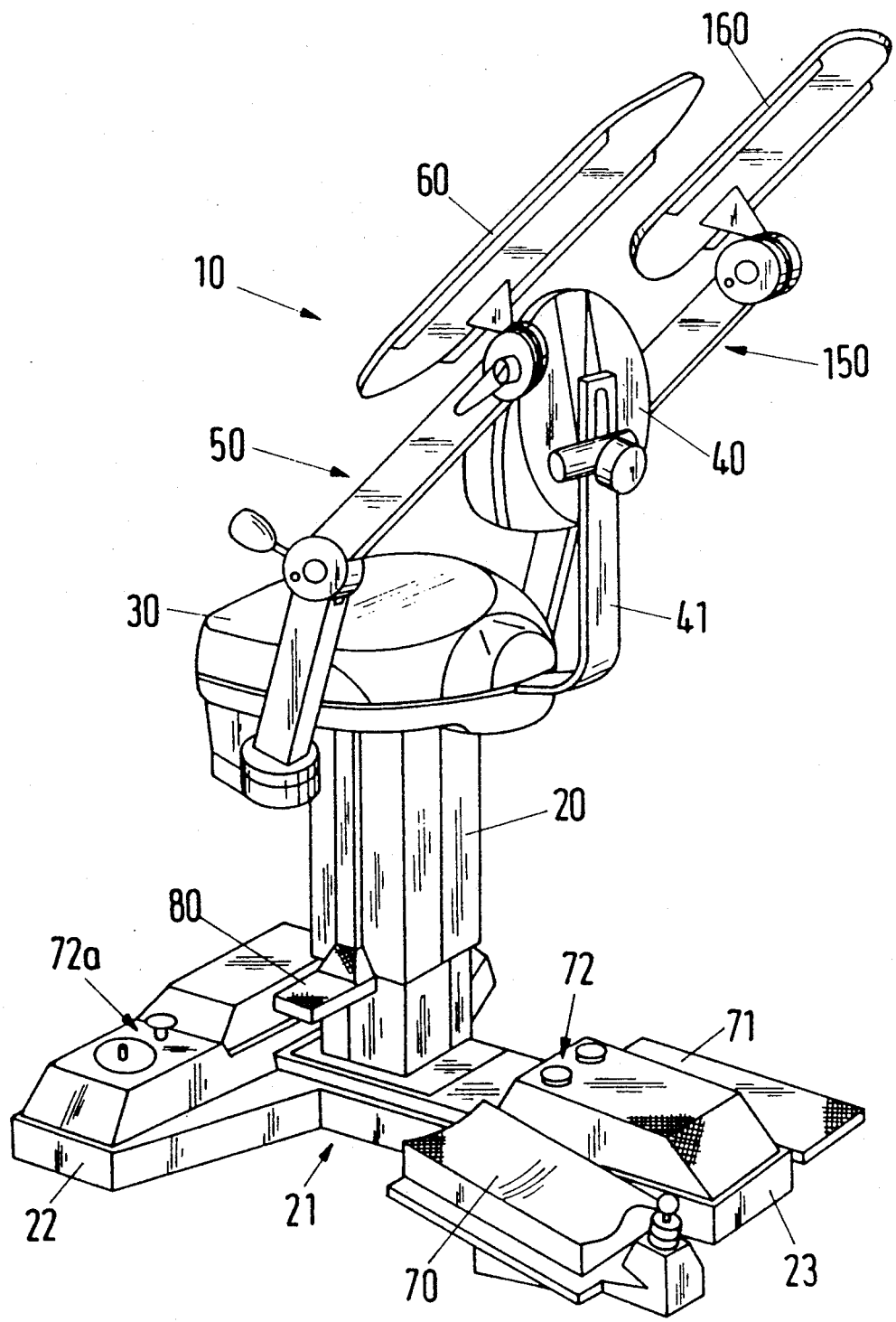
FIG. 5 shows the surgeon's chair with the backrest used as a front rest or support.

In order to be able to use the backrest 40 as a frontrest or chest support, the supporting arm 41 is, with its backrest 40, by means of a plug-type or clamping connection indicated at 35 in FIGS. 1 and 3, detachably and lockably attached to the seat 30 so that, by means of this detachable plug-type or clamping connection 35, the supporting arm 41 can be interchanged with the backrest 40 on the seat 30, as is shown in FIG. 5. For this interchanging of the supporting arm 41 with its backrest 40, the seat 30, on two oppositely located sides, is provided with appropriately constructed adaptors for receiving and arresting the supporting arm 41.

Figure 4:
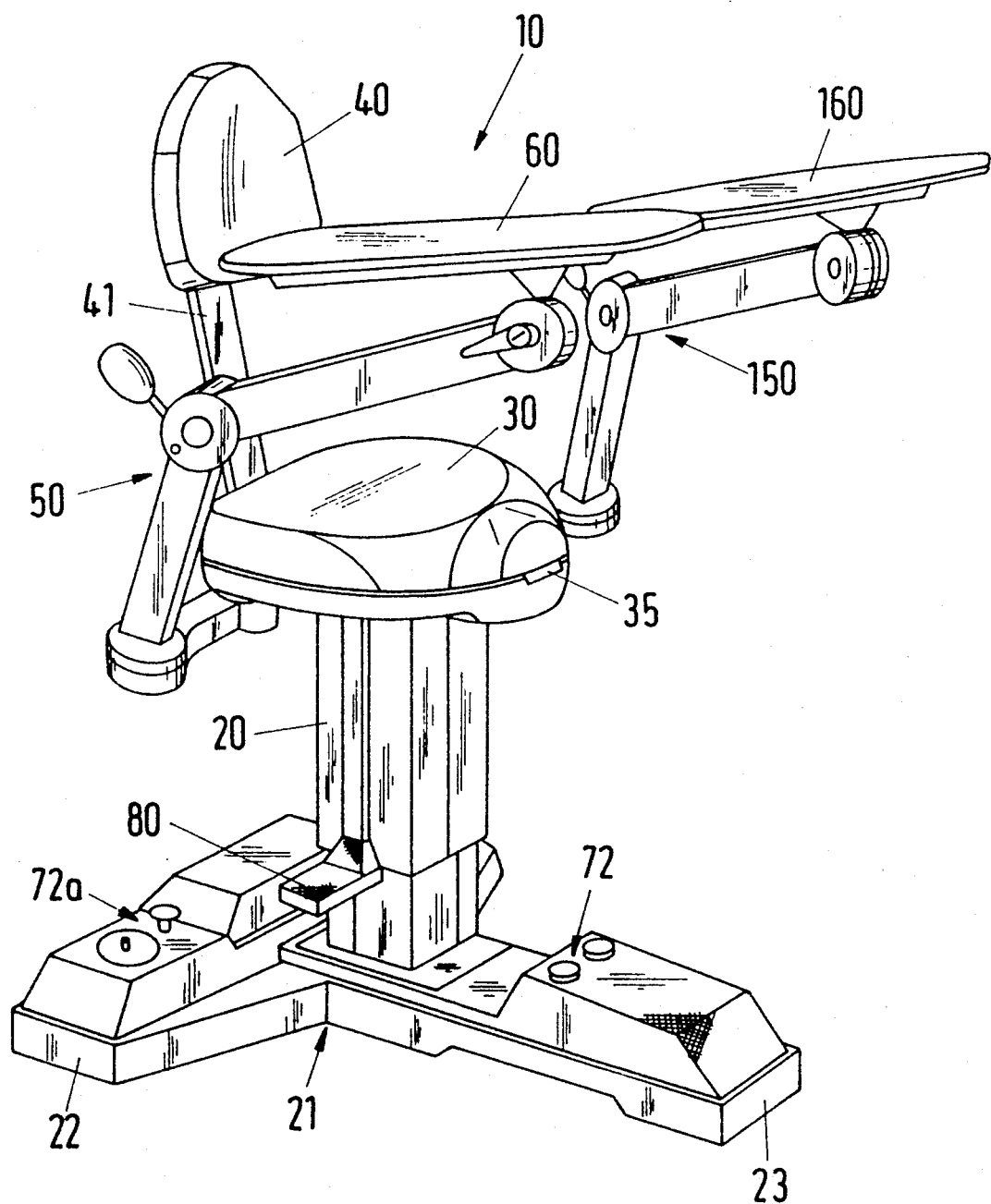
FIG. 4 shows the surgeon's chair according to FIG. 1 without additional foot-operated switches.

In addition, the surgeon's chair 10 according to FIGS. 1, 4 and 5 is fitted with two supporting bars 50,150 disposed on both sides of the seat 30 with armrests 60,160, the supporting bars 50,150 being retained on the seat 30 swivellable within themselves as well as swivellable relative to the seat 30. Both supporting bars 50,150 with their armrests 60,160 are constructed in an identical manner, hence only the supporting bar 50 is described in greater detail in the following.

The supporting bar 50 and thus also the supporting bar 150, is formed by atriculatedly interconnected legs 51,52,53 that can be arrested in every swivel and angular position. The arresting is indicated in FIGS. 1 at 62; the deivices employed for this purpose preferably are of mechanical construction and contructed in the form of locking devices.

Of the legs 51,52,53 of the supporting bar 50, the first leg 51 is hinged with one of its ends 51 on the underside of the seat 30 so as to project horizontally and to be swivellable about a vertical axis 54, a free swivellability exists in this case, however, there also exist the possibility of arresting the swivel position or the angular position of the leg 51 relative to the seat 30. The second leg 52 of the supporting bar 50, relative to the first leg 51, assumes a vertical position or a position at a predetermined angle (FIG. 1). This second leg 52 is, with its one end 52a, arranged on the free end 51b of the first leg 51 so as to be swivellable about the axis 56, however, there also exists the possibility of effecting the fastening in such a way that the second leg 52 is swivellable about a vertical axis on the first leg 51. The third leg 53 of the supporting bar 50, according to FIGS. 1 and 4, assumes an approximately horizontal position and is, with its one end 53a, hinged onto the free end 52b of the second leg 52 and is swivellable about a horizontal axis 55. On its free end 53b, the third leg 53 supports the armrest 60 which is swivellable about a horizontal axis 61 on the free end 53b of the third leg 53 which can be arrested in every swivel position by means of a locking device indicated at 63.

The overall disposition of the two supporting bars 50,150 with their armrests 60,160 is such that the supporting bars with the armrests come to be located on both sides of the seat 30, as appears from FIG. 1 which depicts the surgeon's chair 10 in an initial position of the supporting bars and the armrests. The supporting bars 50,150 with the armrests 60,160 are rigidly or detachably connected to the seat 30. Both supporting bars 50,150 are transferrable into the most widely varied and angular positions desired at any time (FIGS. 1 and 5).

The longitudinal bar 23 of the base 21 is provided with a foot-operated switch 72, with the aid of which the electromotive vertical adjustment and horizontal displacement of the seat 30 can be controlled. This foot-operated switch 72 is integrated into the longitudinal bar 23 of the base 21 and arranged in such a way that it can be located and actuated without difficulty. The transverse bar 22 of the base 21, too, may be additionally provided with a foot-operated and control switch 72a. Over and above that, additional foot-operated switches and control switches 70,71 may be provided if further devices or units have to be controlled. These additional and perhaps also already existing foot-operated switches 70,71 are fitted on the longitudinal bar 23 with the aid of mounting means provided on the longitudinal bar 23 of the base 21 that are not shown in the drawing.

The legs 51,52,53 forming the supporting bars 50,150 may be interconnected by means of their articulated connections in such a way that an automatic locking takes place in each angular position of the legs relative to each other, which is effected e.g. with the aid of spring members or otherwise constructed mechanical means so that a manual locking is not necessary. Also the locking of the respective angular positions of the armrests 60,160 can take place automatically subsequent to the effected adjustment of the nangles of inclination.

What is claimed is:

1. A surgeon's chair, characterized in that the surgeon's chair (10) consists of a vertical column (20), a T-shaped base (21) with a transverse bar (22) and a longitudinal bar (23), a vertically adjustable and horizontally displaceable seat (30) fitted on the upper end (20a) of the column (20), with a rearward supporting arm (41) carrying a vertically adjustable backrest (40), as well as of two supporting bars (50,150) with armrests (60,160) disposed on both sides of the seat (30), in which chair each suporting bar (50;150), at its end underneath the seat (30), is secured to the latter and is formed by three hingedly connected legs (51,52,53) that can be locked in every swivel and angular position, of which the one leg (51) is hinged with its one end (51a) to the underside of the seat (30) while projecting horizontally and is swivellable about a vertical axis (54), the second leg (52) assuming an approximately vertical position or a position at a predetermined angle and disposed so as to be swivellable about the axis (56) with its one end (52a) on the free end of the first leg (51) and the third leg (53) assuming an approximately horizontal position is, with its one end (53a), hinged onto the free end (52b) of the second leg (52) and is swivellable about a horizontal axis (55) and supports the armrest (60) on its free end (53b), which, on the free end (53b) of the third leg (53), is swivellable about a horizontal axis (61) and can be locked in every swivel position (63), both supporting bars (50,150) with their armrests (60,160) being located on both sides of the seat (30), and in that the longitudinal bar (23) of the base (21) is provided with foot-operated switches (72) integrated into the longitudinal bar (23) for an electromotively effected vertical adjustment and a horizontal displacement of the seat (30).

2. A surgeon's chair according to claim 1, wherein the supporting bars (50,150) with the armrests (60, 160) are rigidly or detachably connected to the seat (30)

3. A surgeon's chair according to claims 1, wherein the seat (30) is constructed so as to be horizontally displaceable by means of a horizontal guideway fitted to the upper end (20a) of the column (20) and a carriage constructed on the underside of the seat (30) that is retained slidingly in the guideway.

4. A surgeon's chair according to claim 3, wherein the seat (30) is lockable in every displacement position.

5. A surgeon's chair according to claim 3, wherein an electromotive drive means is provided for the horizontal displacement of the seat (30).

6. A surgeon's chair according to claim 1, wherein the seat (30) is constructed so as to be vertically adjustable with the aid of mechanical means or an electromotive means which can be controlled by a foot-operated switch (72) on the longitudinal bar (23) of the base (21).

7. A surgeon's chair according to claim 1, wherein the supporting arm (41) with the backrest (40) is rigidly or detachably secured to the seat (30) by means of a plug-type or clamping connection and is constructed so as to be interchangeable with the other side of the seat (30), which is provided with a further plug-type or clamping connection.

8. A surgeon's chair according to claim 1, wherein the column (20) is mounted on the longitudinal bar (23)

adjacent to the connecting area of the transverse bar (22) with the longitudinal bar (23).

9. A surgeon's chair according to claim 1, wherein the longitudinal bar (23) of the base (21) is, on both sides, provided with additional foot-operated and control switches (70,71).

10. A surgeon's chair according to claim 1, wherein the base (21) of the surgeon's chair (10) is provided with lockable runners.

* * * * *